United States Patent
Hagan et al.

(10) Patent No.: US 6,884,247 B1
(45) Date of Patent: Apr. 26, 2005

(54) METHODS FOR TREATING OSTEOLYTIC BONE LESIONS

(75) Inventors: Cary P. Hagan, Germantown, TN (US); Harris R. Brian, Cordova, TN (US)

(73) Assignee: Wright Medical Technology Inc., Arlington, TN (US)

( * ) Notice: Subject to any disclaimer, the term of this patent is extended or adjusted under 35 U.S.C. 154(b) by 19 days.

(21) Appl. No.: 10/681,969

(22) Filed: Oct. 9, 2003

(51) Int. Cl.⁷ ................................................ A61B 5/00
(52) U.S. Cl. ................................................... 606/86
(58) Field of Search .............................. 606/86, 92, 93, 606/94; 623/17.11, 17.12, 23.61, 23.62; 604/28, 35, 506

(56) References Cited

U.S. PATENT DOCUMENTS

| | | | |
|---|---|---|---|
| 4,399,814 A | * 8/1983 | Pratt et al. ...................... 606/94 |
| 5,171,244 A | 12/1992 | Caspari et al. |
| 5,228,459 A | 7/1993 | Caspari et al. |
| 5,263,498 A | 11/1993 | Caspari et al. |
| 5,304,181 A | 4/1994 | Caspari et al. |
| 5,376,123 A | * 12/1994 | Klaue et al. .............. 623/23.19 |
| 5,395,376 A | 3/1995 | Caspari et al. |
| 5,693,099 A | * 12/1997 | Harle ....................... 623/23.19 |
| 5,800,383 A | * 9/1998 | Chandler et al. .............. 604/35 |
| 6,325,788 B1 | * 12/2001 | McKay ........................ 604/506 |
| 6,402,758 B1 | * 6/2002 | Tolson .......................... 606/94 |
| 6,622,731 B1 | * 9/2003 | Daniel et al. ................ 128/898 |

FOREIGN PATENT DOCUMENTS

WO    WO91/10408    7/1991

* cited by examiner

*Primary Examiner*—Eduardo C. Robert
*Assistant Examiner*—Annette Reimers
(74) *Attorney, Agent, or Firm*—Shawn D. Sentilles

(57) ABSTRACT

Methods for treating osteolytic bone lesions of all kinds are disclosed. The method includes making two holes in the bone adjacent the lesion and first applying a negative pressure source to one hole and then injecting a flushing fluid into the other. The method also includes replacing the flushing fluid line with a source of, at least, bioimplantable material to fill the void left by the flushed out bone lesion.

6 Claims, 5 Drawing Sheets

METHODS FOR TREATING OSTEOLYTIC BONE LESIONS

FIELD OF THE INVENTION

This invention is generally related to osteolytic bone lesions and more specifically related to osteolytic bone voids that may develop as a result of particulate debris that can collect around orthopedic implants. The invention is exemplified by an embodiment in which an osteolytic bone lesion around an implanted hip stem is treated.

BACKGROUND OF THE INVENTION

It is often seen as inevitable that a patient, having undergone a total hip replacement (at least on the femoral side of the joint), will at a later point in life have to undergo a revision operation. Furthermore, even a revision hip may later need to be further revised. The outcome of each revision surgery typically results in lower quality of life for the patient.

One possible reason the revision may be needed is due to the development of an osteolytic lesion between the implant and adjacent healthy bone. These lesions or bone voids, which are often soft and spongy and not supportive of the implant, can cause a well-fixed implant to loosen. To treat this situation, the old implant is removed, the lesion cleaned out by debriding the local area, and then a larger "revision" implant put in.

This phenomena of osteolytic lesions can occur in many other body locations where implants have previously been implanted, e.g., humerus, tibial plateau (knee), distal femur (knee), acetabulum, etc. Accordingly, the need to treat osteolytic bone lesions after joint replacement surgery can be widespread.

Therefore, there is a continued need for improved treatments for osteolytic lesions. Accordingly, there is room for improvement within the art.

SUMMARY OF THE INVENTION

It is an object of the invention to provide an improved treatment for osteolytic bone lesions.

It is an object of the invention to provide an improved treatment for osteolytic bone lesions that does not require removal of the previous implant.

It is an object of the invention to provide an improved treatment for osteolytic bone lesions, wherein the treatment is a minimally invasive technique.

These and other objects are achieved by a method of treating an osteolytic bone lesion, comprising the steps of: making a first hole in the bone adjacent the bone lesion; making a second hole in the skin and bone adjacent the bone lesion; attaching a source of negative pressure to the second hole; attaching a source of fluid to the first hole; injecting the fluid through the first hole and into the bone; and whereby the fluid mixes with the bone lesion and both the fluid and bone lesion are sucked out of the bone through the second hole, by the negative pressure.

DETAILED DESCRIPTION OF THE DRAWINGS

An exemplary embodiment of a method for treating osteolytic bone voids that meets and achieves the various objects of the invention set forth above will now be described.

Figure 1:
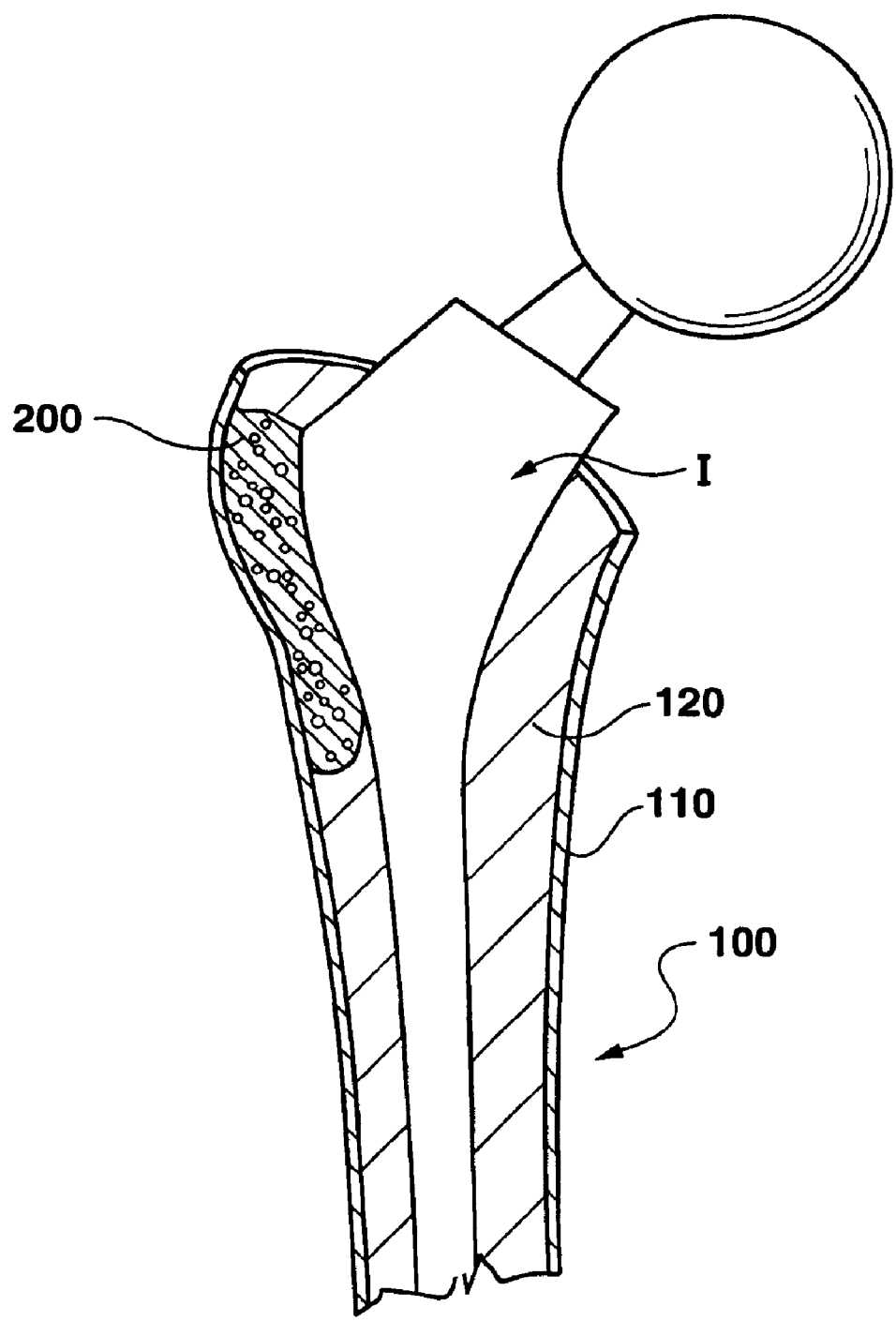
FIG. 1 shows an exemplary body part, namely the proximal femur, subject to osteolysis.

FIG. 1 shows an exemplary body part, namely the proximal femur, subject to osteolysis. This exemplary body part is merely used for convenience. However, the concepts of the instant invention may be applied to any body part undergoing osteolysis, even those that were not subject to prior implant surgery. For example, areas of the body subject to osteolytic bone lesions in the form of unicameral bone cysts may also be treated by the inventive method.

In FIG. 1, a hip implant I has been surgically implanted into the proximal femur (hip) 100. Typically, this surgery will have happened in the past. The details of hip implant I are Irrelevant to the method of this invention and the implant may come in any form, e.g., fixed, modular, primary, revision, ceramic head, metal head, etc.

In non-diseased portions of hip 100, implant I is well-fixed between cortical bone 110 and cancellous bone 120.

In a diseased portion of hip 100, osteolytic lesion 200 takes up space that would normally be filled with cancellous bone 120. Lesion 200 is often soft and spongy. Though lesion 200 is depicted in this exemplary embodiment as being in the area of the proximal stem, it could just as easily have been in the area of the distal stem.

In any event, as lesion 200 will, in most instances be surrounded by at least cancellous bone 120, and usually also cortical bone 110, treatment is significant and invasive because it has previously involved removal of the implant I, debridement of the lesion area (which enlarges the intramedullary area even further), and implantation of the revision implant. This is typically not done as a minimally-invasive procedure.

Applicants have come up with a minimally-invasive approach to treating these lesions that no longer require removal of implants and immediate revision. Accordingly, the patient has a longer period of time between surgeries, undergoes prolonged improved quality of life, etc.

Figure 2:
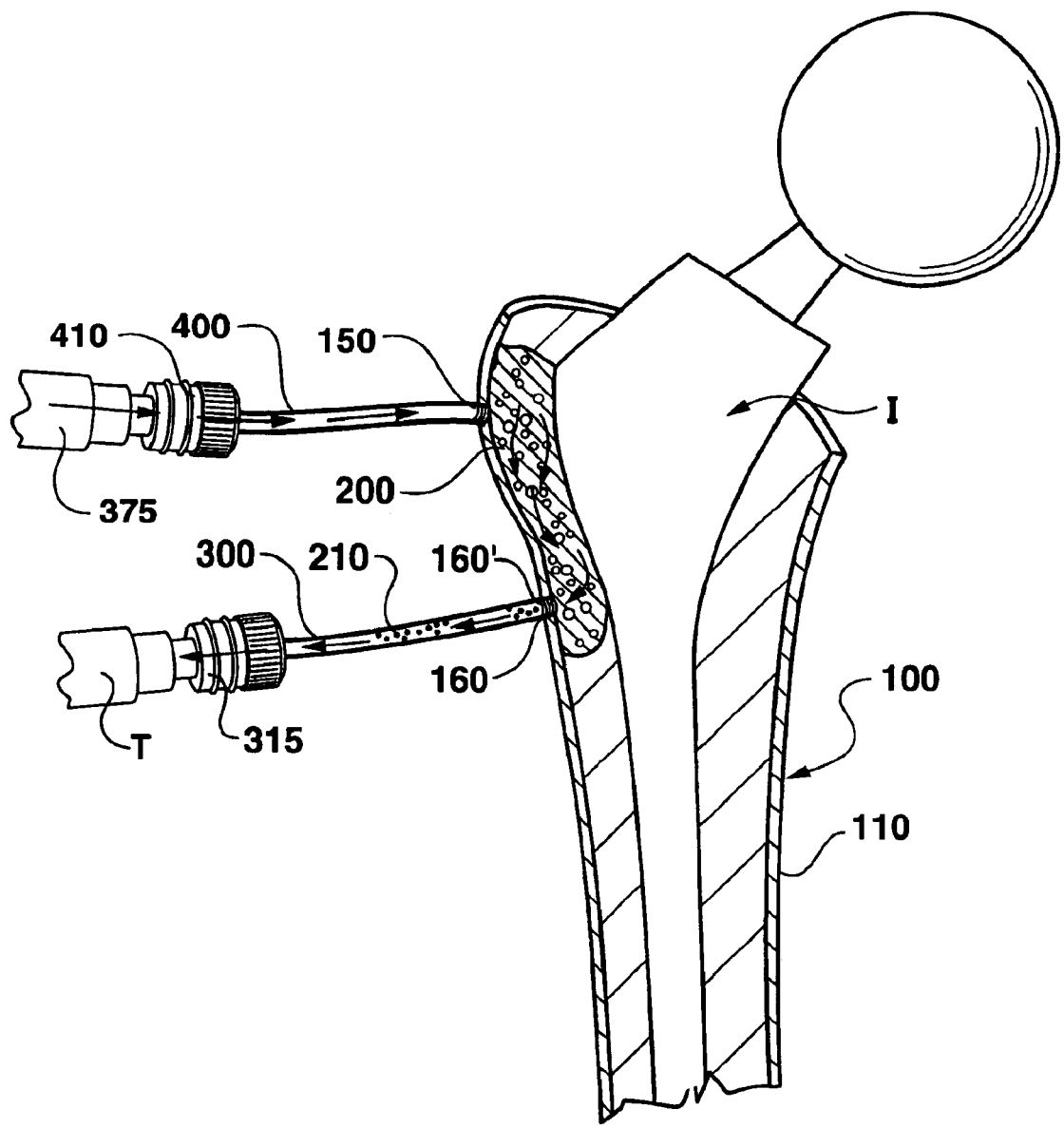
FIG. 2 shows an exemplary body part, namely the proximal femur, subject to osteolysis, and undergoing a step in the process according to the invention.
Figure 3A:
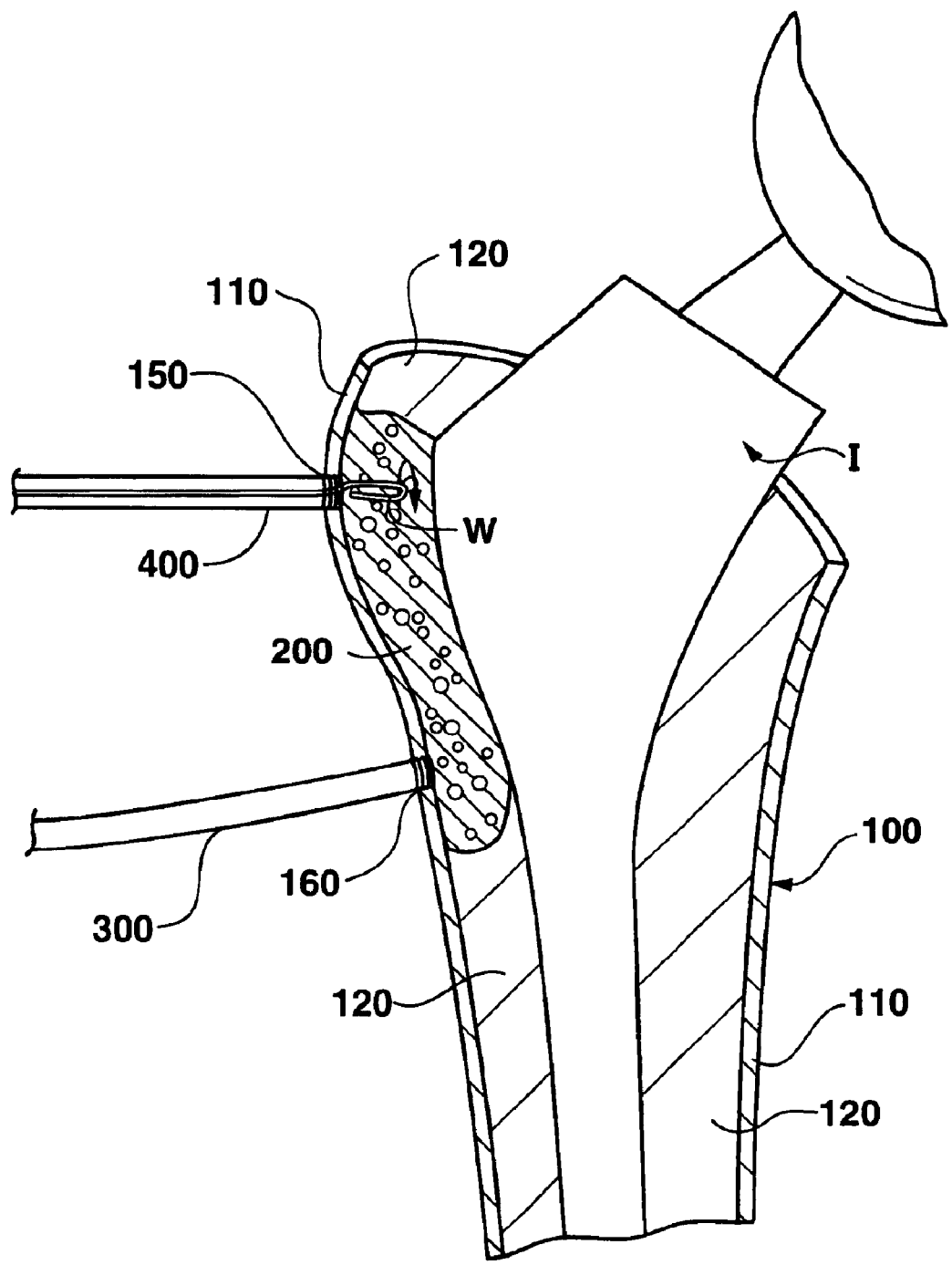
FIG. 3A shows an exemplary body part, namely the proximal femur, subject to osteolysis, and undergoing an optional step in the process according to the invention.
Figure 3B:
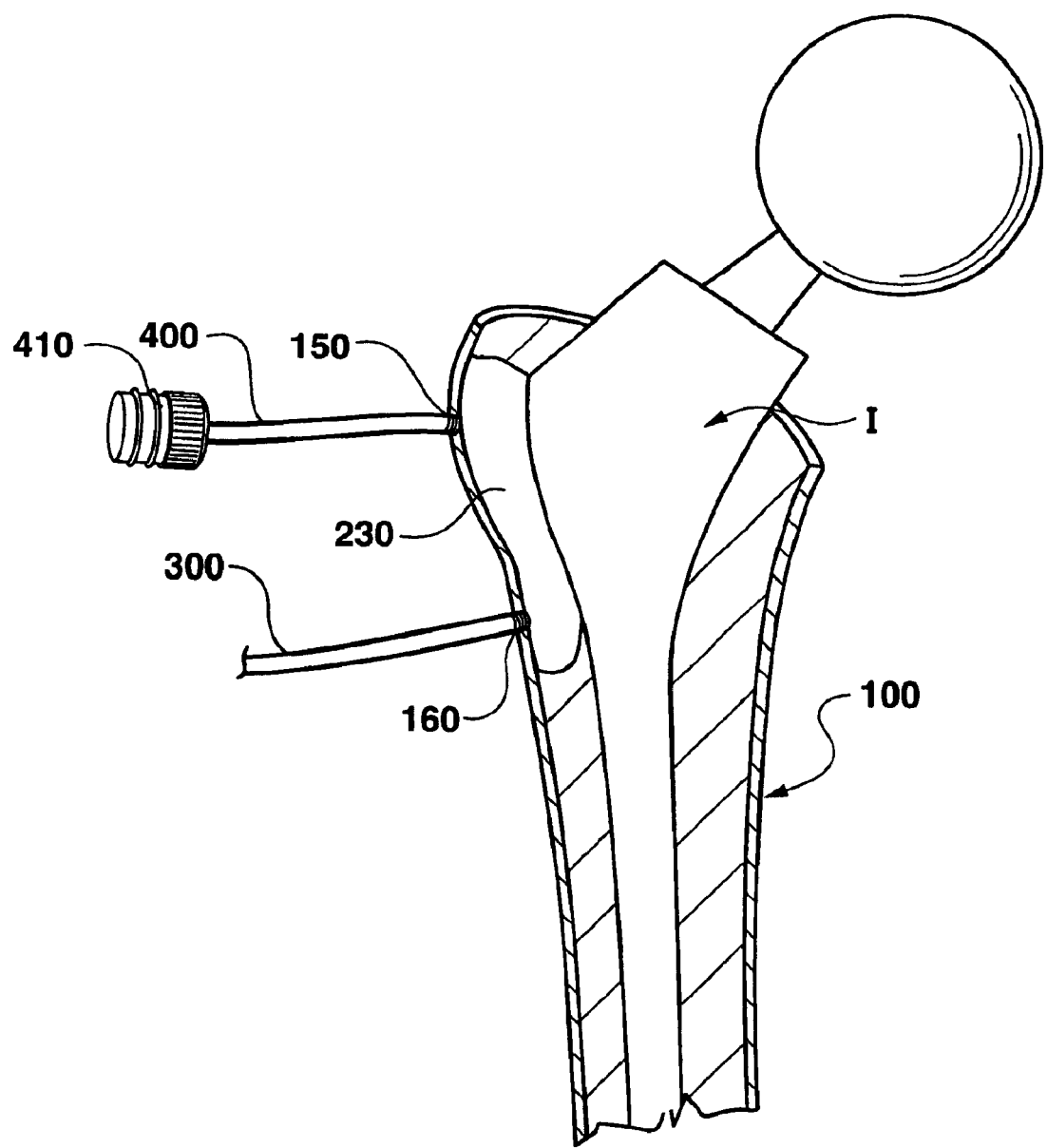
FIG. 3B shows an exemplary body part, namely the proximal femur, subject to osteolysis, and undergoing a step in the process according to the invention.
Figure 4:
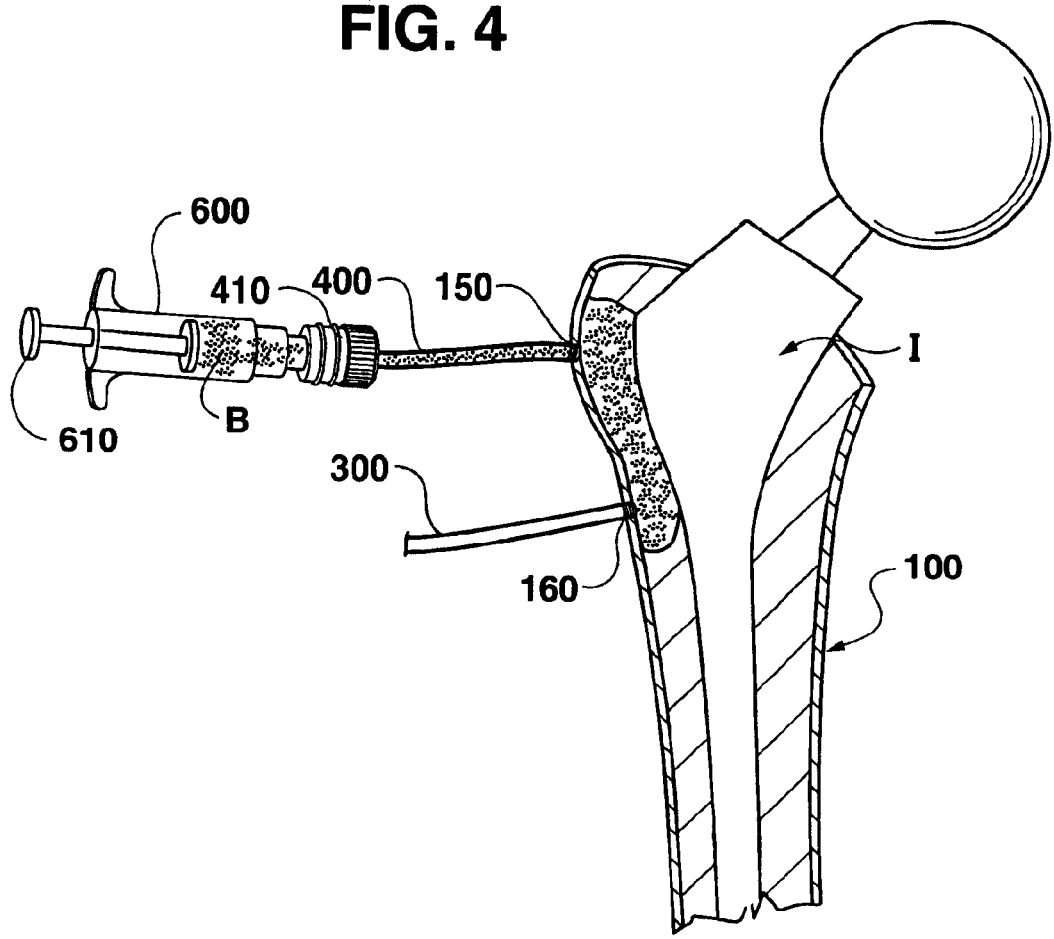
FIG. 4 shows an exemplary body part, namely the proximal femur, subject to osteolysis, and undergoing another step in the process according to the invention.

An exemplary application of the method according to the invention is shown in FIGS. 2–4, with relation to an osteolytic lesion in the hip.

In FIG. 2, after the lesion 200 has been identified by any conventional means (x-ray, fluoroscope, etc.), first and second holes 150 and 160, respectively, are made through the patient's skin (not shown) and cortical bone 110 adjacent the lesion 200.

Figure 5:
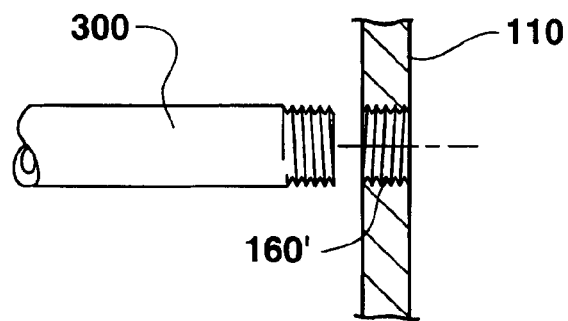
FIG. 5 shows an alternative embodiment of how the various lines can be connected to the bone undergoing the process.

Second hole 160 will be attached/connected to a conventional negative pressure source, such as a suction source (not shown) via suction line 300. Typically, the conventional suction source will be the wall suction. However, the suction source may be any vacuum pump. Furthermore, while suction line 300 will typically be attached to second hole 160 via threads 160' drilled into cortical bone 110, (FIG. 5), there is no such requirement. Suction line 300 may be attached to hole 160 by any means. Though suction line 300 itself will typically be a cannula with a luer lock 315 for further connection to tubing T or a syringe, it may comprise tubing.

First hole 150 will first be attached/connected to a fluid source (not shown) via fluid line 400. Typically, the fluid source will be a saline containing syringe 375. However, the fluid source may be a saline pump. Furthermore, while the fluid has been discussed as saline, it need not be. Any medically accepted fluid useful for flushing clean a lesion site may be used. Fluid line 400 can also be attached to first hole 150 via threads as described with respect to the vacuum line and second hole 160. However, fluid line 400 may be attached to first hole 150 by any means. Though fluid line 400 itself will typically be a cannula with a luer lock for further connection to tubing T or a syringe, it may also comprise tubing.

All cannulae may be radially ported for 360 degree delivery of material, as well as for delivery in an axial direction. Furthermore, for complicated anatomical areas, the cannulae may be positioned using conventional guide wires and fluoroscope.

Fluid is then injected through fluid line 400, through first hole 150, and into the lesion 200 area. Fluid is injected at sufficient pressure that when combined with the suction from suction line 300, the fluid will easily make its way into the lesion area yet not result in the pressurization of the fluid into, for example, nutrient vessels, e.g., emboli. The moving fluid begins to break up the soft lesion 200 and fragments 210 of the lesion 200 become entrained in the fluid. Fluid and entrained lesion fragments 210 begin being sucked out of the bone through the suction line 300. This flow is continued until the suction line 300 is clear of lesion fragments 210.

At this point, optionally, the above process can be repeated with the fluid line 400 attached to second hole 160 and the suction line 300 attached to first hole 150 to provide yet further flushing of the lesion site. Optionally, the process of switching the fluid and negative pressure lines may be repeated multiple times.

Note calling the various holes 150, 160 "first" and "second", is merely for convenience and intended to have no limiting effect. Furthermore, though the suction line 300 is shown as being below the fluid line 400 during the first fragment flush, there is no preferred or required order or orientation and indeed, much depends on the size and shape of the lesion itself. Furthermore, if the two holes are too far apart, it is possible that the fluid pressure inside femur 100 can become excessive causing a fracture of the cortical bone 110.

Finally, in the case of lesions that are not soft and spongy, but dense or containing a membrane, an additional step may be required. As shown in FIG. 3A, a conventional rotating wire wisp W or similar device, will be used to macerate the lesion 200 so that it can be flushed. This wire wisp W can be inserted into the lesion area via either of first or second hole 150, 160, and either of line 300 or 400, and therefore there is no need to prepare another incision or make a larger incision. Minimally invasive surgically devices useful for making cavities inside body tissue are extremely well known, see e.g., U.S. Pub. No. 2003/0055316, U.S. Pat. No. 6,328,251 and patents cited therein, all of which are incorporated by reference herein.

FIG. 3B depicts the post-flushing/macerating stage of the method. The lesion 200 area is now replaced with an empty space/void 230.

FIG. 4 depicts the void-filling stage of the method. During this stage of the method, preferably a bioabsorbable material is introduced through the first hole 150 and into the bone. As will be described below, not only will this material temporarily fill the void, it will also be the source of new bone growth in the void area.

A source of bioabsorbable material B is provided. Typically, bioabsorbable material B will be contained within a conventional syringe 600 having a plunger 610. However, it is possible to use a mechanically-pumped source of material. It is preferred that syringe 600 would be brought into fluid contact with void 230 by connecting the conventional screw end on the end of syringe 600 with the luer cap 410 on the end of fluid line 400. However, it is possible that fluid line 400 can be removed and a needle attached to syringe 600 and the tip of the needle inserted directly into hole 150. The benefit to using fluid line 400 is that it then becomes possible to fill the void with bioabsorbable material from both holes without having to remove the suction line 300 from one hole and move it to the other.

The bioabsorbable material would be injected according to its label instructions and when combined with the suction from suction line 300, will easily make its way into the void area. The injection process may be carried out using fluoroscopic guidance or percutaneously.

The preferred bioabsorbable material B is an injectable form of calcium sulfate ($CaSO_4$) known as MIIG™, sold by Wright Medical Technology, Inc. of Arlington, Tenn., the assignee of the present patent application. This material has superior compressive strengths, completely resorbs, regenerates bone, and is capable of passing through very small gauge needles with manual pressure. The materials underlying this product are described in, for example, U.S. Published Patent Application 2003/0185903.

Other possible bioabsorbable materials may be injectable forms of: calcium phosphate, tri-calcium phosphate, hydroxyapatite, coral hydroxyapatite, demineralized bone matrix, and mineralized bone matrix. Furthermore, the bioabsorbable material may be an injectable form of a biopolymer, for example, polylactic acid, polyglycolic acid, polygalactic acid, polycaprolactone, polyethylene oxide, polypropylene oxide, polysulfone, polyethylene, polypropylene, or hyaluronic acid, bioglass.

Though preferably the material is bioabsorbable, it is also possible that the material be merely bioimplantable, e.g., hydroxyapatite or PMMA. Material selection is based on the application.

Finally, as mentioned with respect to wisp W, it should be noted that prior to the injection of the bioabsorbable material B, it is possible to use arthoscopic shaving tools to go in through either of fluid or suction lines 400, 300 and further clean the lesion site if the doctor so desires. By using injectable biomaterials, eventhough small needle sizes are used, it is still possible to pass arthroscopy tools through them or at least through openings 150 and 160 and therefore not require more invasive surgery.

While the invention has been described with respect to a preferred embodiment and certain variations, the invention is not so limited and reference should be made to the appended claims.

That which is claimed:

1. A method of treating an osteolytic bone lesion, comprising the steps of:

making a first hole in the bone adjacent said bone lesion;

making a second hole in the skin and bone adjacent said bone lesion;

attaching a source of negative pressure to said second hole;

attaching a source of fluid to said first hole;

injecting said fluid through said first hole and into said bone; and whereby said fluid mixes with said bone lesion and both said fluid and bone lesion are sucked out of said bone through said second hole, by said negative pressure.

2. The method according to claim 1, further comprising the steps of, whereby after said fluid and bone lesion are sucked out:

detaching said source of fluid from said first hole;

attaching a source of bioimplantable material to said first hole; and injecting said bioimplantable material through said first hole and into said bone.

3. The method according to claim 2, wherein said bioimplantable material is a bioabsorbable material.

4. The method according to claim 3, wherein said bioabsorbable material includes calcium sulfate.

5. The method according to claim 2, further comprising the step of using an arthroscopic instrument to macerate said bone defect.

6. The method according to claim, 2, wherein said bone lesion further comprises a bone cyst.

* * * * *

UNITED STATES PATENT AND TRADEMARK OFFICE
CERTIFICATE OF CORRECTION

PATENT NO. : 6,884,247 B1
DATED : April 26, 2005
INVENTOR(S) : Cary P. Hagan and Brian R. Harris, Jr.

It is certified that error appears in the above-identified patent and that said Letters Patent is hereby corrected as shown below:

<u>Title page,</u>
Item [75], Inventors, "Harris R. Brian" should read -- Brian R. Harris, Jr. --

Signed and Sealed this

Seventh Day of June, 2005

JON W. DUDAS
*Director of the United States Patent and Trademark Office*